United States Patent [19]
Lindner et al.

[11] Patent Number: 5,160,666
[45] Date of Patent: Nov. 3, 1992

[54] LIQUID PRESERVATIVES

[75] Inventors: Wolfgang Lindner, Seelze; Hans-Ulrich Neuber; Erich Taschenbrecker, both of Wunstorf, all of Fed. Rep. of Germany

[73] Assignee: Riedel-De Haen AG, Seelze, Fed. Rep. of Germany

[21] Appl. No.: 502,859

[22] Filed: Apr. 2, 1990

[30] Foreign Application Priority Data

Apr. 11, 1989 [DE] Fed. Rep. of Germany ....... 3911808

[51] Int. Cl.$^5$ .................. C07G 303/00; A23J 7/00
[52] U.S. Cl. ................... 252/402; 252/403
[58] Field of Search ............ 252/402, 403, 363.5; 524/94, 238

[56] References Cited

U.S. PATENT DOCUMENTS 3,335,108  8/1967  Pines ..................... 524/238
3,393,188  7/1968  Strauss et al. ........... 524/238

OTHER PUBLICATIONS

Chemical Abstracts, vol. 87, 206525e, 1977, pp. 290-291.
Chemical Abstracts, vol. 87, No. 17, "Microbicides for industrial products", (128816), Oct. 24, 1977, p. 217.

Primary Examiner—Kriellion S. Morgan
Attorney, Agent, or Firm—Connolly and Hutz

[57] ABSTRACT

Liquid preservative compositions which are particularly useful for plastics dispersions and secondary products prepared therefrom are disclosed. These compositions comprise mixtures of 1,2-benzisothiazolin-3-one or a salt thereof and at least one alkyl(polyaminoalkyl)glycine compound.

8 Claims, No Drawings

LIQUID PRESERVATIVES

The invention relates to a liquid, alkali-stable industrial preservative which is particularly suitable for preserving aqueous plastics dispersions and secondary products prepared therefrom.

Plastics dispersions (also called synthetic resin dispersions, synthetic resin latices or synthetic resin emulsions) usually contain 0.01 to 2.5 μm of large synthetic resin particles of, for example, polyvinyl acetate, polybutylidene chloride, polyvinyl chloride, polyacrylates or styrene-butadiene copolymers in water, and usually additions of organic solvents and additives. They are used, for example, for the preparation of emulsion paints, emulsion plasters, adhesives, concrete auxiliaries, paper-coating compositions, leather finishes and the like.

Plastics dispersions and secondary products prepared therefrom are attacked by microorganisms and then decomposed microbially. Plastics dispersions, especially the high quality dispersions of low residual monomer content which are sought after for ecotoxic reasons and the secondary products prepared therefrom, must be protected from spoiling by microorganisms during storage. However, no completely satisfactory preservative is as yet available for this, for the plastics dispersions and the secondary products prepared therefrom are adjusted to pH values above 8 to guarantee the colloid stability, and most of the bactericides usually employed in the industrial sector are degraded by hydrolysis in this alkaline range.

The use of 1,2-benzisothiazolin-3-one (below: BIT) for preserving industrial products which have been rendered alkaline is already known. Nevertheless, this active compound has an unbalanced action spectrum against bacteria. Combination products of BIT with other biologically active compounds have therefore already been proposed for preserving industrial products.

Several proposals relate to the combination of BIT with formaldehyde depot substances. Since an equilibrium concentration of free formaldehyde is split off from these formaldehyde depot substances in aqueous solution, their universal use is not possible. There are also toxicological objections to the use of formaldehyde in plastics dispersions. Moreover, because of the ability of formaldehyde to react with other constituents of the formulation to be preserved, discolorations may occur.

The use of so-called amphosurfactants for disinfection of surfaces is also already known (compare S. S. Block, Disinfection, Sterilization and Preservation, 3rd edition (1983), Chapter 16, p. 335 et seq., Verlag Lea+-Febiger, Philadelphia). Amphosurfactants in this context are, in particular, the alkyl(polyaminoalkyl)-glycines known under the tradename Tego ® (Tego ® is a trademark of Goldschmidt, Essen). However, these amphosurfactants cannot be used in the biologically effective use concentration for preserving plastics dispersions, emulsion paints and dispersion adhesives because coagulation of the dispersions occurs.

Japanese Preliminary Published Specification 52-87230, cited in Chemical Abstracts 87: 206525e, relates to antibiotic components which are prepared by mixing alkyl-poly(aminoethyl)-glycine salt and BIT or a salt thereof with one another so that the amount of the former is more than 0.3 times as much as that of the latter. The preservation system is said to be used for preserving emulsion paints, resin emulsions, starch pastes, sizes, shampoos and cleaning agents. However, the preservation system used in the Japanese Preliminary Published Specification is usually not compatible with plastics dispersions and secondary products prepared therefrom because of the high amphosurfactant content, since coagulation occurs by interaction with the emulsifier system. Furthermore, according to the preparation example given, no storage-stable liquid formulation of the active compounds can be prepared.

There is thus a great demand for an alkali-stable, ecotoxically acceptable preservative having a broad action spectrum for industrial products, in particular for those which can be employed in alkaline plastics dispersions, emulsion paints and dispersion adhesives and do not lead to coagulation or thickening in these. The preservative must additionally be available in a storage-stable formulation, since incorporation of the individual components into the dispersion to be preserved is not possible. Such a preservative is provided by the present invention.

The invention thus relates to a liquid preservative, in particular for plastics dispersions and secondary products prepared therefrom, containing a) as component A, 1 to 24.5% by weight of 1,2-benzisothiazolin-3-one or a salt of this compound, b) as component B, 0.1 to 7% by weight of an alkyl(polyaminoalkyl)glycine of the formula I:

$$R-(NH-(CH_2)_n)_m-NH-CH_2-COOH \quad (I)$$

and/or of the formula II:

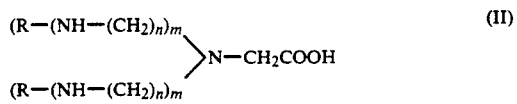

$$\begin{matrix}(R-(NH-(CH_2)_n)_m \\ (R-(NH-(CH_2)_n)_m\end{matrix}\Big\rangle N-CH_2COOH \quad (II)$$

and/or of the formula III

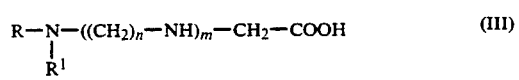

$$R-\underset{R^1}{N}-((CH_2)_n-NH)_m-CH_2-COOH \quad (III)$$

and/or a salt of one of the compounds I, II or III, dissolved in water or in at least one water-miscible solvent or in a mixture of water and at least one water-miscible solvent, wherein the weight ratio of A:B=(3.5 to 100):1 and R denotes $C_8$ to $C_{18}$-alkyl,
$R^1$ denotes $((CH_2)_n-NH)_m-(CH_2)_n-NH_2$,
n denotes 2 to 4 and
m denotes 1, 2, 3, 4 or 5.

The preservative according to the invention contains as component A BIT or a salt of this compound. BIT is commercially available and can be used in the form supplied for the preparation of preservative according to the invention (for example PROXEL ®GXL commercial product and trademark of ICI).

Suitable salts of BIT are above all alkali metal salts of BIT, in particular the lithium, sodium or potassium salt, or ammonium salts of BIT, it being possible for the ammonium to be unsubstituted ($NH_4^+$), or to be formed from a primary, secondary or tertiary amine positively charged on the nitrogen. Such amines preferably contain not more than 6 C atoms.

The lithium and sodium salt of BIT are preferred.

Component A can consist of BIT or a salt of BIT or of BIT and/or one or more salts of BIT.

In the formulae I to III, R represents a $C_8$ to $C_{18}$-alkyl radical, preferably a $C_{10}$ to $C_{14}$-alkyl radical. n preferably denotes 2 or 3 and m preferably denotes 1 or 2.

Component B consists of at least one compound of the formulae I, II or III, but can also consist of a mixture of different compounds of the formulae I and/or II and/or III. Compounds of the formula I, and here in particular those where $n = 3$, are preferred as component B. Compounds of the formula I where $n = 3$ and $m = 1$ are especially preferred as component B.

The alkyl(polyaminoalkyl)glycines of the formulae I to III can form salts with acids, for example mineral acids, such as, for example, hydrogen chloride, hydrogen bromide or sulphuric, nitric or phosphoric acid. The alkyl(polyaminoalkyl)-glycines of the formulae I to III can be employed as such or in their salt form, for example as the hydrochloride, hydrobromide, hydrogen sulphate and/or hydrogen nitrate.

The alkyl(polyaminoalkyl)glycines of the formulae I, II or III and their salts are known and are commercially available under various tradenames (for example Tego ® and Tegol ®, both are trademarks of Goldschmidt, Essen) in the form of aqueous solutions, it being possible for the commercial products to be mixtures of various compounds of the formulae I and/or II and/or III.

The weight ratio between the components A:B in the liquid preservative according to the invention is (3.5 to 100):1, preferably (3.8 to 10):1.

The liquid preservative according to the invention preferably contains 4 to 20% by weight of component A and 0.6 to 5.3% by weight of component B, the weight ratio of A:B especially preferably being (3.8 to 10):1.

In the liquid preservative according to the invention, components A and B are usually dissolved in a mixture of water and one or more water-miscible solvents. However, they can also be dissolved in an organic solvent or solvent mixture or, if the content of component A is not too high, also only in water.

Suitable water-miscible solvents are to be found, for example, in the series of alcohols; ketones; ethers; glycols; di-and polyglycols; polyethylene glycol-polypropylene glycol condensation products; and ethers and esters of glycols, di- and polyglycols and polyethylene glycol-polypropylene glycol condensation products.

Suitable alcohols are, for example, methanol, ethanol, propanol, iso-propanol and tert.-butanol. Suitable ketones are, for example, acetone and methyl ethyl ketone. A suitable ether is, for example, methoxybutanol.

Water-miscible solvents which are employed are above all glycolic solvents, that is to say glycols and ethers and esters thereof, in particular those of the formula IV $$R^2-X-R^3 \qquad (IV)$$

wherein

X denotes the radical of the formula

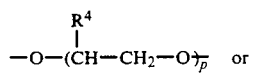

or the radical, bonded via two oxygen atoms, of a polyethylene glycol-polypropylene glycol condensation product, $R^2$ and $R^3$ independently of one another denote hydrogen, $C_1-C_{18}$-alkyl, the acyl radical of a $C_1-C_4$-carboxylic acid or $(C_1-C_{10})$-alkyl-phenyl, $R^4$ denotes hydrogen or methyl and p denotes a number from 1 to 13, preferably 1 to 10.

Examples of suitable compounds of the formula IV are: ethylene glycol, diethylene glycol (=diglycol), triethylene glycol, tetraethylene glycol, polyethylene glycol having a molecular weight up to 600, propylene glycol, dipropylene glycol, tripropylene glycol, polypropylene glycols, monomethyl, -ethyl, -propyl, -i-propyl and -butyl ethers of ethylene gycol, diethylene glycol, propylene glycol and dipropylene glycol, such as, for example, methyl-glycol (=ethylene glycol monomethyl ether), ethyl-glycol, propylglycol, butyl-glycol, methyl-diglycol (diethylene glycol monomethyl ether), ethyl-diglycol and butyldiglycol; di-($C_1$ to $C_4$)-alkyl ethers of ethylene glycol, propylene glycol, diethylene glycol and dipropylene glycol, such as, for example, dimethyl-diglycol (=diethylene glycol dimethyl ether), diethyl-diglycol and dibutyl-diglycol, polyethylene glycol dimethyl ether 250, nonylphenoxypolyethoxyethanol and fatty acid alkoxypolyethoxyethanol.

Other examples of suitable compounds of the general formula IV are esters of ethylene glycol, di-ethylene glycol, propylene glycol and dipropylene glycol, of ($C_1$ to $C_4$)-monoalkyl ethers of ethylene glycol, diethylene glycol and propylene glycol, and of dipropylene glycol with a $C_1$ to $C_4$-carboxylic acid. The carboxylic acid here can be straight-chain or branched and/or saturated or unsaturated. The carboxylic acid is preferably acetic acid. Examples which may be mentioned are: ethylene glycol monoacetate, propylene glycol monoacetate, diethylene glycol monoacetate, dipropylene glycol monoacetate, ethylene glycol diacetate, propylene glycol diacetate, diethylene glycol diacetate, dipropylene glycol diacetate, ethyl-diglycol acetate, butyldiglycol acetate, ethyl-dipropylene glycol acetate and butyldipropylene glycol acetate.

Of the glycolic solvents, ethylene glycol, diethylene glycol or polyethylene glycol or mono- or dialkyl ethers thereof, or propylene glycol, dipropylene glycol or polypropylene glycol or mono- or dialkyl ethers thereof, or the corresponding lower alkyl esters, when alkyl in each case denotes methyl, ethyl, n-propyl, isopropyl or butyl, are usually employed.

Ethylene glycol, propylene glycol, methyldiglycol, butyldiglycol, dipropylene glycol, diethylene glycol and polyethylene glycol (molecular weight 300 to 600) is preferred.

Suitable water-miscible solvents are also those which contain one or more amino groups in the molecule, as long as they do not cause discoloration in the dispersions to be preserved. 2-Amino-methylpropan-1-ol, for example, is suitable.

The pH of the preservative according to the invention is preferably alkaline, and in particular adjusted to pH 8 to 13.5, and is especially preferably 9 to 10.5. The alkaline pH is established by addition of suitable inorganic or organic bases. Suitable inorganic bases are, for example, alkali metal hydroxides, in particular lithium, sodium or potassium hydroxide, and furthermore ammonia. Suitable organic bases are, for example, aliphatic primary, secondary and tertiary amines, such as, for example, triethyl-, di-n-propyl-, tri-n-propyl-, n-butyl-, n-pentyl- and n-hexyl-amine; and furthermore di- and polyamines, such as, for example, ethylenediamine, trimethylenediamine, tetramethylenediamine, pentamethylenediamine and hexamethylenediamine; and furthermore alkanolamines, such as, for example, ethanolamine, diethanolamine and triethanolamine.

However, only those amines which are compatible with the dispersions to be preserved or the secondary products, and in particular cause no discolorations in them, can be used.

The abovementioned amines can also occur in the positively charged form as cations of the BIT of component A.

The abovementioned bases can be employed individually or as a mixture with one another, as such or in the form of solutions, in particular aqueous solutions, for establishing the alkaline pH in the liquid preservatives according to the invention. 2 to 6% by weight of alkali metal hydroxide, based on the finished preservative, are usually required to establish a pH of 8 to 13.5.

To prepare the preservative according to the invention, components A and B, preferably in the form of their commercial products, are mixed with one another, which can be effected, for example, by stirring, in water or in a water-miscible solvent or solvent mixture, if appropriate with addition of water. To accelerate the dissolution of the BIT, it may be advantageous to carry out the mixing at an elevated temperature of, for example, up to 60° C. During mixing, components A and B are mixed with water and/or the solvent or solvent mixture in a weight ratio such that the abovementioned percentages by weight and weight ratios of components A and B are obtained in the finished preservative.

The base or base mixture is also added in bulk or in the form of a solution during the preparation in order to establish the alkaline pH.

If appropriate, one or more other constituents, thus, for example, one or more wetting agents or non-ionic surfactants and/or one or more water-miscible thickening agents, such as, for example, maleic acid copolymers, and/or one or more other biocidally active compounds, can also additionally be added during the preparation.

The preservatives according to the invention are alkalistable and are used for preventing the growth of microorganisms in industrial products, in particular in alkaline industrial products. To preserve acid, neutral or alkaline industrial products, in particular aqueous plastics dispersions, and aqueous formulations of plastics dispersions, such as, for example, emulsion paints, dispersion plasters, dispersion adhesives, concrete auxiliaries, paper-coating compositions, leather finishes and the like, a preservative according to the invention is added to the product to be preserved.

The preservatives according to the invention can likewise be used for protecting naturally occurring products, such as, for example, starch and casein sizes, gelatine, cellulose and the like. They can likewise be employed for preserving surfactant solutions, oil emulsions, wax emulsions and the like.

Surprisingly, the preservatives according to the invention have a better action against moulds and bacteria than was to be expected from the sum of the activity of the individual components. That is to say, the preservatives according to the invention have a synergistically increased activity. Moreover, they surprisingly cause no precipitation when added to alkaline industrial products. They can be incorporated in the plastics dispersions, even of the pure acrylate or styrene acrylate type and copolymers thereof, without coagulation of the dispersions occurring. On the basis of their compatibility, they can thus be employed particularly effectively for preserving aqueous plastics dispersions and secondary products.

Suitable aqeuous plastics dispersions which can be preserved using the preservatives according to the invention are in principle all the dispersions which have been prepared by polymerization or copolymerization of $\alpha,\beta$-unsaturated compounds in the aqueous phase, and the secondary products prepared therefrom.

The dispersions and the secondary products prepared therefrom can contain the customary amounts of additives, such as fillers, thickeners, plasticizers, corrosion inhibitors, pigments, foam suppressants and other substances.

The preservative according to the invention can be added at any time during the preparation process of the industrial product to be preserved. It is particularly advantageous to add the preservative immediately after preparation of the industrial product, uniform distribution being ensured by stirring However, the preservatives according to the invention can also be added as a mixture with an auxiliary which is in any case added for preparation of the industrial product.

For preservation, a preservative according to the invention is incorporated in a concentration of 0.002 to 0.11% by weight, preferably 0.006 to 0.065% by weight (in each case based on the sum of the active substances A and B), into the industrial products to be preserved.

Particularly preferred preservatives according to the invention contain 5 to 15% by weight of component A, 1 to 3.9% by weight of component B, the weight ratio of components A:B being (3.8 to 10):1, and 65 to 75% by weight of a glycolic solvent, in particular ethylene glycol, 5 to 20% by weight of water and a base which adjusts the pH to 9 to 10.5.

The present invention is illustrated further by the following examples, in which parts and percentage contents are expressed by parts by weight and percentages by weight.

EXAMPLE 1

124.5 g of a water-moist press-cake of crude 1,2-benzisothiazoline-3-one (BIT) (content 75%, remainder water) are introduced into a mixture of 100 g of Tegol ® 2000 (24% of dodecylaminopropylglycine hydrochloride, remainder water), 83 g of sodium hydroxide solution (32% strength) and 692.5 g of ethylene glycol, while stirring. The mixture is stirred at 50° C. until a clear solution is present. A storage-stable formulation containing 9.3% of 1,2-benzisothiazolin-3-one, 2.1% of 1-dodecylaminopropylglycine, 69% of ethylene glycol, 2.4% of sodium hydroxide and 0.4% of sodium chloride, the remainder being water, is obtained.

The formulation has a pH of 9.8 and is storage-stable. This was tested at room temperature, at $-5°$ C. and at 50° C.

Formulations according to the invention of the following Examples 2 to 8 can be prepared in a manner analogous to that in Example 1. These examples have the same storage stability as Example 1.

EXAMPLE 2

Recipe:
108.1 g of BIT (content 86%, remainder water)

200.1 g of Tego ® 103 S
38.0 g of potassium hydroxide (lozenges)
600.0 g of 1,2-propylene glycol
54.0 g of water
Composition of the preservative:
9.3% of 1,2-benzisothiazolin-3-one, 1.6% of 1-dodecyl-1,4,7-triazaoctane-8-carboxylic acid, 0.2% of N,N-didodecyl-3-carboxymethyl-3-azapentylene-1,5-diamine, 60% of 1,2-propylene glycol, 3.5% of potassium hydroxide and 0.4% of potassium chloride, the remainder being water; pH: 12.9.

EXAMPLE 3

Recipe:
116.3 g of BIT (content 86%, remainder water)
200.0 g of Tego ® 103 G
29.1 g of sodium hydroxide (lozenges)
600.0 g of 1,2-propylene glycol
54.6 g of water
Composition of the preservative:
10.0% of 1,2-benzisothiazolin-3-one, 1.6% of 1-$C_{10}$ to $C_{14}$-alkyl-1,4,7-triazaoctane-8-carboxylic acid, 0.2% of N,N-di-$C_{10}$ to $C_{14}$-alkyl-3-carboxymethyl-3-azapentylene-1,5-diamine, 60% of 1,2-propylene glycol, 0.3% of sodium chloride and 2.7% of sodium hydroxide, the remainder being water; pH: 12.8.

EXAMPLE 4

Recipe:
24.7 g of BIT (content 73%, remainder water)
9.9 g of Tego ® 103 G
5.4 g of sodium hydroxide (lozenges)
60.0 g of dipropylene glycol
Composition of the preservative:
18% of 1,2-benzisothiazolin-3-one, 0.8% of 1-$C_{10}$ to $C_{14}$-alkyl-1,4,7-triazaoctane-8-carboxylic acid, 0.1% of N,N-di-$C_{10}$ to $C_{14}$-alkyl-3-carboxymethyl-3-azapentylene-1,5-diamine, 60% of dipropylene glycol, 0.1% of sodium chloride and 5.4% of sodium hydroxide, the remainder being water; pH: 12.5.

EXAMPLE 5

Recipe:
10.8 g of BIT (content 86%, remainder water)
11.7 g of an aqueous solution containing 20% of $C_{10}$–$C_{14}$-alkyl-1,5-diazahexane-6-carboxylic acid as the hydrochloride
8.5 g of sodium hydroxide solution (32% strength)
69.0 g of methyldiglycol
Composition of the preservative:
9.3% of 1,2-benzisothiazolin-3-one, 2.1% of 1-$C_{10}$ to $C_{14}$-alkyl- 1,5-diazahexane-6-carboxylic acid, 69% of methyldiglycol, 0.4% of sodium hydroxide and 2.4% of sodium chloride, the remainder being water; pH: 11.0.

EXAMPLE 6

Recipe:
248.0 g of BIT (content 75%, remainder water)
142.6 g of an aqueous solution containing 20% of 1-dodecyl-1,5,9-triazadecane-10-carboxylic acid as the hydrochloride
169.2 g of sodium hydroxide solution (32% strength)
1200.0 g of 1,2-propylene glycol
240.2 g of water
Composition of the preservative:
9.3% of 1,2-benzisothiazolin-3-one, 1.3% of 5-dodecyl-1,5,9-triazadecane-10-carboxylic acid, 60% of 1,2-propylene glycol, 0.2% of sodium chloride and 2.6% of sodium hydroxide, the remainder being water; pH: 10.5.

EXAMPLE 7

Recipe:
140.0 g of BIT (content 75%, remainder water)
124.3 g of Tego ® 103 S
30.6 g of sodium hydroxide (lozenges)
333.1 g of 2-amino-2-methylpropan-1-ol (content 90%, remainder water)
Composition of the preservative:
10.5% of 1,2-benzisothiazolin-3-one, 1.0% of 1-dodecyl-1,4,7-triazaoctane-8-carboxylic acid, 0.1% of N,N-didodecyl-3-carboxymethyl-3-azapentylene-1,5-diamine, 30% of 2-amino-2-methylpropan-1-ol, 0.2% of sodium chloride and 2.9% of sodium hydroxide, the remainder being water; pH: 12.9.

EXAMPLE 8

Recipe:
20.0 g of BIT (content 75%, remainder water)
14.7 g of TEGOL ® 2000
14.9 g of sodium hydroxide solution (32% strength)
950.4 g of water
Composition of the preservative:
1.5% of 1,2-benzisothiazolin-3-one
0.26% of 1-dodecyl-1,5-diazahexane-6-carboxylic acid
0.5% of sodium hydroxide,
the remainder being water; pH: 11.7.

EXAMPLE 9

This example shows the compatibility of the preservatives according to the invention with a styrene acrylate plastics dispersion.

The compatibility of a preservative with a plastics dispersion is determined as follows: 2 g of the preservative are dissolved in 100 g of water and 1 g of ammonia solution (25% strength). This solution is stirred homogeneously with 100 g of the plastics dispersion. The mixture is left to stand in a closed vessel at 25° C. for two days. It is then decanted in each case in succession through a sieve of 0.08 and 0.056 mm mesh width. The solution which has been sieved clear is stored in a closed vessel at 50° C. for a further 3 days and the sieving operation is then repeated. In each case the amount of sieve residue is rated in comparison with a blank sample without preservative.

The compatibility is summarized in the following table: the preservatives according to the invention do not coagulate the dispersion under the measurement conditions.

| Preservative | Amount of coarse-particled contents | | | |
|---|---|---|---|---|
| | after 2 days | | after 5 days | |
| | Sieve 0.08 mm | Sieve 0.056 mm | Sieve 0.08 mm | Sieve 0.056 mm |
| according to Example 1 | <0.1 g | <0.1 g | <0.1 g | <0.1 g |
| according to Example 2 | <0.1 g | <0.1 g | <0.1 g | <0.1 g |
| according to Example 4 | <0.1 g | <0.1 g | <0.1 g | <0.1 g |
| Comparison Example (Tego ® 103 G) | >1 g | >1 g | not measured | |
| Blank sample (no preservative) | <0.1 g | <0.1 g | <0.1 g | <0.1 g |

EXAMPLE 10

The compatibility of the preservatives according to the invention with a pure acrylate dispersion Mowilith ® DM 772 (Hoechst) (pH 8.8) is tested in a manner analogous to that in Example 9.

| Preservative | Amount of coarse-particled contents | | | |
|---|---|---|---|---|
| | after 2 days | | after 5 days | |
| | Sieve 0.08 mm | Sieve 0.056 mm | Sieve 0.08 mm | Sieve 0.056 mm |
| according to Example 1 | <0.1 g | <0.1 g | <0.1 g | <0.1 g |
| according to Example 2 | <0.1 g | <0.1 g | <0.1 g | <0.1 g |
| according to Example 4 | <0.1 g | <0.1 g | <0.1 g | <0.1 g |
| Comparison Example (Tegol ® 2000) | >1 g | >1 g | not measured | |
| Comparison Example (Embodiment Example 1 from JP 52/87230 15% of Proxel ® CRL (5% of BIT) 60% of Tego ® 51 (18% of amphosurfactant) remainder water) | >1 g | >1 g | not measured | |
| Blank sample (no preservative) | <0.1 g | <0.1 g | <0.1 g | <0.1 g |

EXAMPLE 11

This example shows the compatibility of the preservatives according to the invention with an emulsion paint. A commercially available wall paint is used as the test paint. 0.5 g of the preservative to be tested is homogeneously distributed in 99.5 g of the emulsion paint by stirring. The paint is then stored at 40° C. in a sealed container for 4 weeks. For evaluation, the viscosity of the paint is measured at the start and at the end of storage. No change in viscosity (for example thickening) of the emulsion paint should occur and no coagulation should be detectable by addition of the preservative.

| Preservative | Viscosity | | Coagulation |
|---|---|---|---|
| | Initial value | after 4 weeks | |
| according to Example 1 | 15 · 10³ mPa · s | 15 · 10³ mPa · s | no |
| according to Example 4 | 15 · 10³ mPa · s | 15 · 10³ mPa · s | no |
| Comparison Example (Tegol ® 2000) | 15 · 10³ mPa · s | >50 · 10³ mPa · s | yes |
| Blank sample (no preservative) | 15 · 10³ mPa · s | 15 · 10³ mPa · s | no |

EXAMPLE 12

This example demonstrates the synergistic increase in action of a preservative according to the invention.

Comparative testing of the minimum inhibitory concentration (MIC values) is carried out in a series dilution test using a standard I nutrient broth to which $10^3$ bacteria per ml have been added. After incubation at 37° C. for 48 hours, the MIC values are read off in % based on the formulations employed, each with an active substance content of 11.8%. That concentration at which no clouding of the broth can be detected is specified as the MIC value.

The following values are obtained:

| Preservative | MIC value | |
|---|---|---|
| | Escherichia coli | Pseudomonas aeruginosa DSM |
| According to Example 3 (10.0% of BIT 1.6% of 1-$C_{10}$-$C_{14}$-alkyl-1,4,7-triazaoctane-8-carboxylic acid 0.2% of N,N-$C_{10}$-$C_{14}$-alkyl-3-carboxymethyl-3-azapentylene-1,5-diamine) | 0.020% | 0.050% |
| Comparison Example (10.5% of 1-$C_{10}$-$C_{14}$-alkyl-1,4,7-triazaoctane-8-carboxylic acid 1.3% of N,N-$C_{10}$-$C_{14}$-alkyl-3-carboxymethyl-3-azapentylene-1,5-diamine remainder water, hydrochloric acid) | 0.040% | 0.080% |
| Comparison Example (11.8% of BIT 73% of dipropylene glycol remainder water, sodium hydroxide) | 0.030% | 0.100% |

EXAMPLE 13

This example shows the activity of a preservative according to the invention for preserving a styrene acrylate dispersion Mowilith ® LDM 7770 (Hoechst) (pH 8.8).

In the, modified preservative loading test (compare K. H. Wallhäuer, W. Fink; Farbe+Lack, Volume 91 (1985), pages 277 et seq./397 et seq.), about 10:test germs are stirred into the dispersion to be tested. Subcultures of decayed emulsion paint and Pseudomonas aeruginosa DSM are used as the test germs. After an action time of 7 days, the number of germs which survive after 0.2 g of the dispersion has been brushed onto a cast nutrient plate and incubated for 3 days is determined. The inoculation is repeated after 8 days if only slight microbial growth, if any, is detected in the sample. The inoculation cycle is repeated three times.

The growth on the cast nutrient plate is rated in a scale from 0 to 4 according to the following plan:
0 = no growth
1 = 1-10 germs (very slight growth)
2 = 11-100 germs (slight growth)
3 = more than 100 germs but not yet continuous growth
4 = continuous area of growth The results are summarized in the following table:

| Preservative | Concentration in % | Number of inoculations | | | |
|---|---|---|---|---|---|
| | | 0 | 1 | 2 | 3 |
| According to Example 1 (9.3% of BIT 2.1% of 1-dodecyl-1,5-diazahexane-6-carboxylic acid) | 0.06 | 0 | 1 | 3 | 4 |
| According to Example 1 (9.3% of BIT 2.1% of 1-dodecyl-1,5-diazahexane-6-carboxylic acid) | 0.08 | 0 | 1 | 2 | 3 |
| According to Example 1 (9.3% of BIT 2.1% of 1-dodecyl-1,5-diazahexane-6-carboxylic acid) | 0.10 | 0 | 0 | 1 | 1 |
| According to Example 1 (9.3% of BIT 2.1% of 1-dodecyl-1,5-diazahexane-6-carboxylic acid) | 0.12 | 0 | 0 | 0 | 0 |
| According to Example 1 (9.3% of BIT | 0.15 | 0 | 0 | 0 | 0 |

-continued

| Preservative | Concentration in % | Number of inoculations | | | |
|---|---|---|---|---|---|
| | | 0 | 1 | 2 | 3 |
| 2.1% of 1-dodecyl-1,5-diazahexane-6-carboxylic acid) | | | | | |
| Comparison Example (11.4% of BIT 73% of dipropylene glycol remainder water, sodium hydroxide) | 0.10 | 0 | 2 | 4 | 4 |
| Comparison Example (11.4% of BIT 73% of dipropylene glycol remainder water, sodium hydroxide) | 0.20 | 0 | 2 | 2 | 2 |
| Blank sample no preservative | — | 0 | 4 | 4 | 4 |

EXAMPLE 14

This example shows the activity of a preservative according to the invention for preserving a styrene acrylate dispersion (pH 8.9).

Testing was carried out as described in Example 13 and the results are summarized in the following table:

| Preservative | Concentration in % | Number of inoculations | | | |
|---|---|---|---|---|---|
| | | 0 | 1 | 2 | 3 |
| According to Example 1 (9.3% of BIT 2.1% of 1-dodecyl-1,5-diazahexane-6-carboxylic acid) | 0.10 | 0 | 0 | 0 | 0 |
| According to Example 1 (9.3% of BIT 2.1% of 1-dodecyl-1,5-diazahexane-6-carboxylic acid) | 0.20 | 0 | 0 | 0 | 0 |
| Comparison Example (Mergal ® K 9 N commercially available preservative based on 5-chloro-2-methyl-iso-thiazolin-3-one) | 0.20 | 0 | 0 | 2 | 2 |
| Blank sample no preservative | — | 2 | 4 | 4 | 4 |

EXAMPLE 15

This example shows the activity of a preservative according to the invention for preserving a concrete liquefier (pH 9.8).

Testing was carried out as described in Example 13 and the results are summarized in the following table:

| Preservative | Concentration in % | Number of inoculations | | | |
|---|---|---|---|---|---|
| | | 0 | 1 | 2 | 3 |
| According to Example 1 (9.3% of BIT 2.1% of 1-dodecyl-1,5-diazahexane-6-carboxylic acid) | 0.10 | 0 | 0 | 0 | 0 |
| According to Example 1 (9.3% of BIT 2.1% of 1-dodecyl-1,5-diazahexane-6-carboxylic acid) | 0.20 | 0 | 0 | 0 | 0 |
| Comparison Example (9.3% of BIT 65.0% of 1,3,5-trishydroxyethyl-hexahydrotriazine remainder water, sodium hydroxide) | 0.10 | 1 | 1 | 1 | 3 |
| Comparison Example (9.3% of BIT 65% of 1,3,5-trishydroxyethyl-hexahydrotriazine remainder water, sodium hydroxide) | 0.20 | 0 | 0 | 0 | 2 |
| Blank sample no preservative | — | 4 | 4 | 4 | 4 |

What is claimed is:

1. A liquid preservative composition comprising
   A. 1 to 24.5 % by weight of 1,2-benzisothiazolin-3-one or a salt of this compound,
   B. 0.1 to 7 % by weight of an alkyl(polyaminoalkyl)-glycine compound or mixtures thereof having the following formula I:

$$R-(NH-(CH_2)_n)_m-NH-CH_2-COOH \qquad (I)$$

or formula II:

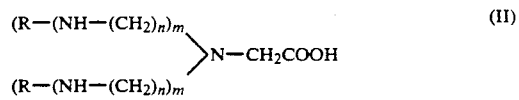

$$(II)$$

or formula III:

$$R-\underset{R^1}{N}-((CH_2)_n-NH)_m-CH_2-COOH \qquad (III)$$

or a salt of one of the compounds of formula I, II or III, dissolved in water or in at least one water-miscible solvent or in a mixture of water and at least one water-miscible solvent, wherein the weight ratio of A:B is 3.5 to 100:1 and
R denotes $C_8$ to $C_{18}$-alkyl,
$R^1$ denotes $((CH_2)_n-NH)_m-(CH_2)_n-NH_2$,
n denotes 2, 3 or 4 and
m denotes 1, 2, 3, 4 or 5.

2. A composition according to claim 1, having an alkaline pH.

3. A composition according to claim 1 having a pH from 8 to 13.5.

4. A composition according to claim 1 wherein R denotes a $C_{10}$ to $C_{14}$-alkyl radical, n denotes 2 or 3 and m denotes 1 or 2.

5. A composition according to claim 1, characterized in that it contains, as component B, a compound of the formula I and wherein n denotes 3 and m denotes 1.

6. A composition according to claim 1 wherein the weight ratio of A:B is 3.8 to 10:1.

7. A composition according to claim 1 characterized in that it contains, as a water miscible solvent, a glycolic solvent of the formula IV $$R^2-X-R^3 \qquad (IV)$$

wherein
X denotes the radical of the formula

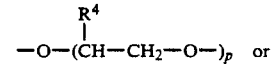

the radical, bonded via two oxygen atoms, of a polyethylene glycolpolypropylene glycol condensation product,
$R^2$ and $R^3$ independently of one another denote hydrogen, $C_1-C_{18}$-alkyl, the acyl radical of a $C_1-C_4$-carboxylic acid or $(C_1-C_{10})$-alkyl phenyl,
$R^4$ denotes hydrogen or methyl and
p denotes a number from 1 to 13.

8. A composition according to claim 1 containing 5 to 15% by weight of a component A, 1 to 3.9% by weight of component B, the weight ratio of A:B being 3.8 to 10:1 and 65 to 75% by weight of a glycolic solvent, 5 to 20% by weight of water and a pH of 9 to 10.5.

* * * * *